(12) United States Patent
Dassler et al.

(10) Patent No.: US 8,053,211 B2
(45) Date of Patent: Nov. 8, 2011

(54) **PROCESS FOR THE FERMENTATIVE PRODUCTION OF HETEROLOGOUS PROTEINS BY MEANS OF *ESCHERICHIA COLI***

(75) Inventors: Tobias Dassler, Munich (DE); Simone Mitterweger, Gilching (DE); Guenter Wich, Munich (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 12/641,447

(22) Filed: Dec. 18, 2009

(65) Prior Publication Data

US 2010/0221776 A1 Sep. 2, 2010

(30) Foreign Application Priority Data

Dec. 19, 2008 (DE) .......................... 10 2008 063 900

(51) Int. Cl.
*C12P 21/06* (2006.01)
*C12P 15/00* (2006.01)
*C12N 1/20* (2006.01)

(52) U.S. Cl. .................. 435/69.1; 435/252.3; 435/320.1

(58) Field of Classification Search ................. 435/69.1, 435/252.3, 320.1
See application file for complete search history.

(56) References Cited

U.S. PATENT DOCUMENTS 5,919,895 A 7/1999 Schmid et al.
2008/0076157 A1 3/2008 Leonhartsberger et al.
2008/0254511 A1 10/2008 Dassler et al.

FOREIGN PATENT DOCUMENTS

EP 0 448 093 A2 9/1991
WO 9859043 A 12/1998

OTHER PUBLICATIONS

Concepcion et al., J. Bacterilogy, 2003, 185(2), 444-452.*
Gentry, Daniel R. et al, "Mutational analysis of the *Escherichia coli* spoT gene identifies distinct but overlapping regions involved in ppGpp synthesis and degradation," Mol. Microbiol. (1996), 19(6), pp. 1373-1384.
Skerra, Arne, "A general vector, pASK84, for cloning, bacterial production, and single-step purification of antibody Fab fragments," Gene, 141 (1994), pp. 79-84.
Simmons, Laura C. et al, "Expression of full-length immunoglobulins in *Escherichia coli*: rapid and efficient production of aglycosylated antibodies," J. Immunol. Methods, (2002), 263, pp. 133-147.
Gitter, B. et al., "Influence of stringent and relaxed response on excretion of recombinant proteins and fatty acid composition in *Escherichia coli*.," Appl. Microbiol. Biotechnol., (1995), 43, pp. 89-92.
Choi, J.H. et al., "Secretory and extracellular production of recombinant proteins using *Escherichia coli*," Appl. Microbiol. Biotechnol., (2004), 64, pp. 625-635.
Shokri, A. et al., "Cell and process design for targeting of recombinant protein into the culture medium of *Escherichia coli*," Appl. Microbiol. Biotechnol., (2003), 60, pp. 654-664.
Link, Andrew J. et al., "Methods for Generating Precise Deletions and Insertions in the Genome of Wild-Type *Escherichia coli*: Application to Open Reading Frame Characterization," J. Bacteriol., (1997), pp. 6228-6237.
Durfee, Tim et al., "The Complete Genome Sequence of *Escherichia coli* DH10B: Insights into the Biology of a Laboratory Workhorse," J. Bacteriol., (2008), pp. 2597-2606.
Metzger, Shula et al., "Characterization of the relA1 Mutation and a Comparison of relA1 with New relA Null Alleles in *Escherichia coli*," J. Biol. Chem., (1989), v. 264, n. 35, pp. 21146-21152.
Chang, Jui-Yoa, "Stability of Hirudin, a Thrombin-specific Inhibitor," J. Biol. Chem., (1991), v. 266, n. 17, pp. 10839-10843.
Xiao, Hua et al., "Residual Guanosine 3',5'-Bispyrophosphate Synthetic Activity of RelA Null Mutants Can be Eliminated by spoT Null Mutations," J. Biol. Chem., (1991), v. 266, n. 9, pp. 5980-5990.
Datsenko, K.A. et al., "One-step inactivation of chromosomal genes in *Escherichia coli* K-12 using PCR products," PNAS, (2000), v. 97, n. 12, pp. 6640-6645.
Mechold, Undine et al, "Functional Analysis of relA/spoT Gene Homolog from *Streptococcus equisimilis*," J. Bacteriol., (1996), 178, pp. 1401-1411.
Cashel, M. et al., "The Stringent Respose," *Escherichia coli* and *Salmonella* Cellular and Molecular Biology, (1996) ed. Neidhardt, F.C. ASM Press, Washington, D.C., pp. 1458-1496.
Dedhia, N. et al., "Improvement in Recombinant Protein Production in ppGpp-Deficient *Excherichia Coli*," Biotechnology and Engineering, vol. 53, No. 4, 20. Feb. 1997, pp. 379-386.

* cited by examiner

*Primary Examiner* — Maryam Monshipouri
(74) *Attorney, Agent, or Firm* — Brooks Kushman P.C.

(57) ABSTRACT

A process for producing a heterologous protein is provided. The process comprises culturing an *E. coli* strain in a fermentation medium, the *E. coli* strain harboring a gene which codes for the heterologous protein and is functionally linked to a signal sequence coding for a signal peptide, and releasing the heterologous protein into the fermentation medium, and the heterologous protein being removed from the fermentation medium, wherein the *E. coli* strain has an attenuated (p)ppGpp-synthetase II activity (PSII activity).

7 Claims, No Drawings

SEQUENCE LISTING

```
<160> NUMBER OF SEQ ID NOS: 17

<210> SEQ ID NO 1
<211> LENGTH: 2109
<212> TYPE: DNA
<213> ORGANISM: Escherichia coli
<220> FEATURE:
<221> NAME/KEY: gene
<222> LOCATION: (1)..(2109)
<223> OTHER INFORMATION: spoT-Gen (Wildtyp)
<300> PUBLICATION INFORMATION:
<301> AUTHORS: Sarubbi, Edoardo
<302> TITLE: Characterization of the spoT gene of Escherichia coli.
<303> JOURNAL: J. Biol. Chem.
<304> VOLUME: 264
<305> ISSUE: 25
<306> PAGES: 15074-15082
<307> DATE: 1989

<400> SEQUENCE: 1
ttgtatctgt tgaaagcct gaatcaactg attcaaacct acctgccgga agaccaaatc      60
aagcgtctgc ggcaggcgta tctcgttgca cgtgatgctc acgaggggca aacacgttca     120
```

```
agcggtgaac cctatatcac gcacccggta gcggttgcct gcattctggc cgagatgaaa      180
ctcgactatg aaacgctgat ggcggcgctg ctgcatgacg tgattgaaga tactcccgcc      240
acctaccagg atatggaaca gcttttggt  aaaagcgtcg ccgagctggt agaggggtg       300 tcgaaacttg ataaactcaa gttccgcgat aagaagagg  cgcaggccga aactttcgc       360 aagatgatta tggcgatggt gcaggatatc cgcgtcatcc tcatcaaact tgccgaccgt      420
acccacaaca tgcgcacgct gggctcactt cgcccggaca aacgtcgccg catcgcccgt      480
gaaactctcg aaatttatag cccgctggcg caccgtttag gtatccacca cattaaaacc      540
gaactcgaag agctgggttt tgaggcgctg tatcccaacc gttatcgcgt aatcaaagaa      600
gtggtgaaag ccgcgcgcgg caaccgtaaa gagatgatcc agaagattct ttctgaaatc      660
gaagggcgtt tgcaggaagc gggaataccg tgccgcgtca gtggtcgcga agcatcttt       720 tattcgattt actgcaaaat ggtgctcaaa gagcagcgtt ttcactcgat catggacatc      780
tacgctttcc gcgtgatcgt caatgattct gacacctgtt atcgcgtgct gggccagatg      840
cacagcctgt acaagccgcg tccgggccgc gtgaaagact atatcgccat tccaaaagcg      900
aacggctatc agtctttgca cacctcgatg atcggcccgc acggtgtgcc ggttgaggtc      960
cagatccgta ccgaagatat ggaccagatg gcggagatgg gtgttgccgc gcactgggct      1020
tataaagagc acggcgaaac cagtactacc gcacaaatcc gcgcccagcg ctggatgcaa      1080
agcctgctgg agctgcaaca gagcgccggt agttcgtttg aatttatcga gagcgttaaa      1140
tccgatctct cccggatga  gatttacgtt ttcacaccgg aagggcgcat tgtcgagctg      1200
cctgccggtg caacgcccgt cgacttcgct tatgcagtgc ataccgatat cggtcatgcc      1260
tgcgtgggcg cacgcgttga ccgccagcct taccgctgt  cgcagccgct taccagcggt      1320
caaaccgttg aaatcattac cgctccgggc gctcgcccga atgccgcttg gctgaacttt      1380
gtcgttagct cgaaagcgcg cgccaaaatt cgtcagttgc tgaaaaacct caagcgtgat      1440
gattctgtaa gcctgggccg tcgtctgctc aaccatgctt gggtggtag  ccgtaagctg      1500 aatgaaatcc gcaggaaaa  tattcagcgc gagctggatc gcatgaagct ggcaacgctt      1560
gacgatctgc tggcagaaat cggacttggt aacgcaatga gcgtggtggt cgcgaaaaat      1620
ctgcaacatg gggacgcctc cattccaccg gcaacccaaa gccacggaca tctgcccatt      1680
aaaggtgccg atggcgtgct gatcacccttt gcgaaatgct gccgccctat tcctggcgac      1740
ccgattatcg cccacgtcag ccccggtaaa ggtctggtga tccaccatga atcctgccgt      1800
aatatccgtg gctaccagaa agagccagag aagtttatgc ctgtggaatg ggataaagag      1860
acggcgcagg agttcatcac cgaaatcaag gtggagatgt tcaatcatca gggtgcgctg      1920
gcaaacctga cggcggcaat taacaccacg acttcgaata ttcaaagttt gaatacggaa      1980
gagaaagatg gtcgcgtcta cagcgccttt attcgtctga ccgctcgtga ccgtgtgcat      2040
ctggcgaata tcatgcgcaa aatccgcgtg atgccagacg tgattaaagt cacccgaaac      2100
cgaaattaa                                                             2109
```

<210> SEQ ID NO 2
<211> LENGTH: 702
<212> TYPE: PRT
<213> ORGANISM: Escherichia coli
<220> FEATURE:
<221> NAME/KEY: PEPTIDE
<222> LOCATION: (1)..(702)
<223> OTHER INFORMATION: SpoT-Protein (Wildtyp)

<400> SEQUENCE: 2

```
Leu Tyr Leu Phe Glu Ser Leu Asn Gln Leu Ile Gln Thr Tyr Leu Pro
  1               5                  10                 15

Glu Asp Gln Ile Lys Arg Leu Arg Gln Ala Tyr Leu Val Ala Arg Asp
             20                  25                 30

Ala His Glu Gly Gln Thr Arg Ser Ser Gly Pro Tyr Ile Thr His
             35                  40                 45

Pro Val Ala Val Ala Cys Ile Leu Ala Glu Met Lys Leu Asp Tyr Glu
         50                  55                 60

Thr Leu Met Ala Ala Leu Leu His Asp Val Ile Glu Asp Thr Pro Ala
 65              70                  75                 80

Thr Tyr Gln Asp Met Glu Gln Leu Phe Gly Lys Ser Val Ala Glu Leu
                 85                  90                 95

Val Glu Gly Val Ser Lys Leu Asp Lys Leu Lys Phe Arg Asp Lys Lys
             100                 105                110

Glu Ala Gln Ala Glu Asn Phe Arg Lys Met Ile Met Ala Met Val Gln
             115                 120                125

Asp Ile Arg Val Ile Leu Ile Lys Leu Ala Asp Arg Thr His Asn Met
         130                 135                140

Arg Thr Leu Gly Ser Leu Arg Pro Asp Lys Arg Arg Ile Ala Arg
145              150                 155                160

Glu Thr Leu Glu Ile Tyr Ser Pro Leu Ala His Arg Leu Gly Ile His
             165                 170                 175

His Ile Lys Thr Glu Leu Glu Glu Leu Gly Phe Glu Ala Leu Tyr Pro
             180                 185                 190

Asn Arg Tyr Arg Val Ile Lys Glu Val Val Lys Ala Ala Arg Gly Asn
             195                 200                 205

Arg Lys Glu Met Ile Gln Lys Ile Leu Ser Glu Ile Glu Gly Arg Leu
             210                 215                 220

Gln Glu Ala Gly Ile Pro Cys Arg Val Ser Gly Arg Glu Lys His Leu
225              230                 235                240

Tyr Ser Ile Tyr Cys Lys Met Val Leu Lys Glu Gln Arg Phe His Ser
             245                 250                 255

Ile Met Asp Ile Tyr Ala Phe Arg Val Ile Val Asn Asp Ser Asp Thr
             260                 265                 270

Cys Tyr Arg Val Leu Gly Gln Met His Ser Leu Tyr Lys Pro Arg Pro
             275                 280                 285

Gly Arg Val Lys Asp Tyr Ile Ala Ile Pro Lys Ala Asn Gly Tyr Gln
             290                 295                 300

Ser Leu His Thr Ser Met Ile Gly Pro His Gly Val Pro Val Glu Val
305              310                 315                 320

Gln Ile Arg Thr Glu Asp Met Asp Gln Met Ala Glu Met Gly Val Ala
             325                 330                 335

Ala His Trp Ala Tyr Lys Glu His Gly Glu Thr Ser Thr Thr Ala Gln
             340                 345                 350

Ile Arg Ala Gln Arg Trp Met Gln Ser Leu Leu Glu Leu Gln Gln Ser
             355                 360                 365

Ala Gly Ser Ser Phe Glu Phe Ile Glu Ser Val Lys Ser Asp Leu Phe
             370                 375                 380

Pro Asp Glu Ile Tyr Val Phe Thr Pro Glu Gly Arg Ile Val Glu Leu
385              390                 395                 400

Pro Ala Gly Ala Thr Pro Val Asp Phe Ala Tyr Ala Val His Thr Asp
             405                 410                 415

Ile Gly His Ala Cys Val Gly Ala Arg Val Asp Arg Gln Pro Tyr Pro
```

```
                        420             425             430
Leu Ser Gln Pro Leu Thr Ser Gly Gln Thr Val Glu Ile Ile Thr Ala
            435                 440                 445

Pro Gly Ala Arg Pro Asn Ala Ala Trp Leu Asn Phe Val Val Ser Ser
        450                 455                 460

Lys Ala Arg Ala Lys Ile Arg Gln Leu Leu Lys Asn Leu Lys Arg Asp
465                 470                 475                 480

Asp Ser Val Ser Leu Gly Arg Arg Leu Leu Asn His Ala Leu Gly Gly
                    485                 490                 495

Ser Arg Lys Leu Asn Glu Ile Pro Gln Glu Asn Ile Gln Arg Glu Leu
                500                 505                 510

Asp Arg Met Lys Leu Ala Thr Leu Asp Asp Leu Leu Ala Glu Ile Gly
            515                 520                 525

Leu Gly Asn Ala Met Ser Val Val Ala Lys Asn Leu Gln His Gly
        530                 535                 540

Asp Ala Ser Ile Pro Pro Ala Thr Gln Ser His Gly His Leu Pro Ile
545                 550                 555                 560

Lys Gly Ala Asp Gly Val Leu Ile Thr Phe Ala Lys Cys Cys Arg Pro
                    565                 570                 575

Ile Pro Gly Asp Pro Ile Ile Ala His Val Ser Pro Gly Lys Gly Leu
                580                 585                 590

Val Ile His His Glu Ser Cys Arg Asn Ile Arg Gly Tyr Gln Lys Glu
            595                 600                 605

Pro Glu Lys Phe Met Ala Val Glu Trp Asp Lys Glu Thr Ala Gln Glu
        610                 615                 620

Phe Ile Thr Glu Ile Lys Val Glu Met Phe Asn His Gln Gly Ala Leu
625                 630                 635                 640

Ala Asn Leu Thr Ala Ala Ile Asn Thr Thr Thr Ser Asn Ile Gln Ser
                    645                 650                 655

Leu Asn Thr Glu Glu Lys Asp Gly Arg Val Tyr Ser Ala Phe Ile Arg
                660                 665                 670

Leu Thr Ala Arg Asp Arg Val His Leu Ala Asn Ile Met Arg Lys Ile
            675                 680                 685

Arg Val Met Pro Asp Val Ile Lys Val Thr Arg Asn Arg Asn
        690                 695                 700

<210> SEQ ID NO 3
<211> LENGTH: 704
<212> TYPE: PRT
<213> ORGANISM: Escherichia coli
<220> FEATURE:
<221> NAME/KEY: PEPTIDE
<222> LOCATION: (1)..(704)
<223> OTHER INFORMATION: SpoT-Protein (SpoT1-Variante)

<400> SEQUENCE: 3

Leu Tyr Leu Phe Glu Ser Leu Asn Gln Leu Ile Gln Thr Tyr Leu Pro
 1               5                  10                  15

Glu Asp Gln Ile Lys Arg Leu Arg Gln Ala Tyr Leu Val Ala Arg Asp
                20                  25                  30

Ala His Glu Gly Gln Thr Arg Ser Ser Gly Glu Pro Tyr Ile Thr His
            35                  40                  45

Pro Val Ala Val Ala Cys Ile Leu Ala Glu Met Lys Leu Asp Tyr Glu
        50                  55                  60

Thr Leu Met Ala Ala Leu Leu His Asp Val Ile Glu Asp Thr Pro Ala
65                  70                  75                  80
```

-continued

```
Thr Tyr Gln Asp Gln Asp Met Glu Gln Leu Phe Gly Lys Ser Val Ala
            85                  90                  95
Glu Leu Val Glu Gly Val Ser Lys Leu Asp Lys Leu Lys Phe Arg Asp
            100                 105                 110
Lys Lys Glu Ala Gln Ala Glu Asn Phe Arg Lys Met Ile Met Ala Met
            115                 120                 125
Val Gln Asp Ile Arg Val Ile Leu Ile Lys Leu Ala Asp Arg Thr His
        130                 135                 140
Asn Met Arg Thr Leu Gly Ser Leu Arg Pro Asp Lys Arg Arg Arg Ile
145                 150                 155                 160
Ala Arg Glu Thr Leu Glu Ile Tyr Ser Pro Leu Ala His Arg Leu Gly
                165                 170                 175
Ile His His Ile Lys Thr Glu Leu Glu Glu Leu Gly Phe Glu Ala Leu
                180                 185                 190
Tyr Pro Asn Arg Tyr Arg Val Ile Lys Glu Val Val Lys Ala Ala Arg
            195                 200                 205
Gly Asn Arg Lys Glu Met Ile Gln Lys Ile Leu Ser Glu Ile Glu Gly
        210                 215                 220
Arg Leu Gln Glu Ala Gly Ile Pro Cys Arg Val Ser Gly Arg Glu Lys
225                 230                 235                 240
His Leu Tyr Ser Ile Tyr Cys Lys Met Val Leu Lys Glu Gln Arg Phe
                245                 250                 255
Tyr Ser Ile Met Asp Ile Tyr Ala Phe Arg Val Ile Val Asn Asp Ser
                260                 265                 270
Asp Thr Cys Tyr Arg Val Leu Gly Gln Met His Ser Leu Tyr Lys Pro
            275                 280                 285
Arg Pro Gly Arg Val Lys Asp Tyr Ile Ala Ile Pro Lys Ala Asn Gly
        290                 295                 300
Tyr Gln Ser Leu His Thr Ser Met Ile Gly Pro His Gly Val Pro Val
305                 310                 315                 320
Glu Val Gln Ile Arg Thr Glu Asp Met Asp Gln Met Ala Glu Met Gly
                325                 330                 335
Val Ala Ala His Trp Ala Tyr Lys Glu His Gly Glu Thr Ser Thr Thr
                340                 345                 350
Ala Gln Ile Arg Ala Gln Arg Trp Met Gln Ser Leu Leu Glu Leu Gln
            355                 360                 365
Gln Ser Ala Gly Ser Ser Phe Glu Phe Ile Glu Ser Val Lys Ser Asp
        370                 375                 380
Leu Phe Pro Asp Glu Ile Tyr Val Phe Thr Pro Glu Gly Arg Ile Val
385                 390                 395                 400
Glu Leu Pro Ala Gly Ala Thr Pro Val Asp Phe Ala Tyr Ala Val His
                405                 410                 415
Thr Asp Ile Gly His Ala Cys Val Gly Ala Arg Val Asp Arg Gln Pro
                420                 425                 430
Tyr Pro Leu Ser Gln Pro Leu Thr Ser Gly Gln Thr Val Glu Ile Ile
            435                 440                 445
Thr Ala Pro Gly Ala Arg Pro Asn Ala Ala Trp Leu Asn Phe Val Val
        450                 455                 460
Ser Ser Lys Ala Arg Ala Lys Ile Arg Gln Leu Leu Lys Asn Leu Lys
465                 470                 475                 480
Arg Asp Asp Ser Val Ser Leu Gly Arg Arg Leu Leu Asn His Ala Leu
                485                 490                 495
Gly Gly Ser Arg Lys Leu Asn Glu Ile Pro Gln Glu Asn Ile Gln Arg
            500                 505                 510
```

```
Glu Leu Asp Arg Met Lys Leu Ala Thr Leu Asp Asp Leu Ala Glu
            515                 520                 525

Ile Gly Leu Gly Asn Ala Met Ser Val Val Ala Lys Asn Leu Gln
530                 535                 540

His Gly Asp Ala Ser Ile Pro Pro Ala Thr Gln Ser His Gly His Leu
545                 550                 555                 560

Pro Ile Lys Gly Ala Asp Gly Val Leu Ile Thr Phe Ala Lys Cys Cys
                565                 570                 575

Arg Pro Ile Pro Gly Asp Pro Ile Ala His Val Ser Pro Gly Lys
            580                 585                 590

Gly Leu Val Ile His His Glu Ser Cys Arg Asn Ile Arg Gly Tyr Gln
            595                 600                 605

Lys Glu Pro Glu Lys Phe Met Ala Val Glu Trp Asp Lys Glu Thr Ala
610                 615                 620

Gln Glu Phe Ile Thr Glu Ile Lys Val Glu Met Phe Asn His Gln Gly
625                 630                 635                 640

Ala Leu Ala Asn Leu Thr Ala Ala Ile Asn Thr Thr Ser Asn Ile
                645                 650                 655

Gln Ser Leu Asn Thr Glu Glu Lys Asp Gly Arg Val Tyr Ser Ala Phe
                660                 665                 670

Ile Arg Leu Thr Ala Arg Asp Arg Val His Leu Ala Asn Ile Met Arg
                675                 680                 685

Lys Ile Arg Val Met Pro Asp Val Ile Lys Val Thr Arg Asn Arg Asn
690                 695                 700

<210> SEQ ID NO 4
<211> LENGTH: 90
<212> TYPE: DNA
<213> ORGANISM: Klebsiella pneumoniae
<220> FEATURE:
<223> OTHER INFORMATION: CGTase-Signalsequenz

<400> SEQUENCE: 4
atgaaaagaa accgtttttt taatacctcg gctgctattg ccatttcgat tgcattaaat    60
actttttttt gtagcatgca gacgattgct                                    90

<210> SEQ ID NO 5
<211> LENGTH: 90
<212> TYPE: DNA
<213> ORGANISM: Artificial Sequence
<220> FEATURE:
<223> OTHER INFORMATION: Description of Artificial Sequence: Variante
      der CGTase-Signalsequenz von K. pneumoniae

<400> SEQUENCE: 5
atgaaaagaa accgtttttt taatacctcg gctgctattg ccatttcgat tgcattacag    60
atcttttttc cgtccgcttc cgctttcgct                                    90

<210> SEQ ID NO 6
<211> LENGTH: 70
<212> TYPE: DNA
<213> ORGANISM: Artificial Sequence
<220> FEATURE:
<223> OTHER INFORMATION: Description of Artificial Sequence:
      Oligonukleotid relAmut-fw

<400> SEQUENCE: 6
atggttgcgg taagaagtgc acatatcaat aaggctggtg aatttgatcc atgggaatta    60
gccatggtcc                                                          70
```

<210> SEQ ID NO 7
<211> LENGTH: 70
<212> TYPE: DNA
<213> ORGANISM: Artificial Sequence
<220> FEATURE:
<223> OTHER INFORMATION: Description of Artificial Sequence:
      Oligonukleotid relAmut-rev

<400> SEQUENCE: 7
ctaactcccg tgcaaccgac gcgcgtcgat aacatccggc acctggttga gtgtaggctg    60
gagctgcttc                                                          70

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence:
      Oligonukleotid relA-fw

<400> SEQUENCE: 8
cattgtagat acgagc                                                   16

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence:
      Oligonukleotid relA-rev

<400> SEQUENCE: 9
gatttcggca ggtct                                                    15

<210> SEQ ID NO 10
<211> LENGTH: 70
<212> TYPE: DNA
<213> ORGANISM: Artificial Sequence
<220> FEATURE:
<223> OTHER INFORMATION: Description of Artificial Sequence:
      Oligonukleotid spoTmut-fw

<400> SEQUENCE: 10
ttgtatctgt ttgaaagcct gaatcaactg attcaaacct acctgccgga atgggaatta    60
gccatggtcc                                                          70

<210> SEQ ID NO 11
<211> LENGTH: 70
<212> TYPE: DNA
<213> ORGANISM: Artificial Sequence
<220> FEATURE:
<223> OTHER INFORMATION: Description of Artificial Sequence:
      Oligonukleotid spoTmut-rev

<400> SEQUENCE: 11
ttaatttcgg tttcgggtga ctttaatcac gtctggcatc acgcggattt gtgtaggctg    60
gagctgcttc                                                          70

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:
      Oligonukleotid spoT-fw

```
<400> SEQUENCE: 12
aatcacaaag cgggtcg                                                    17

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence:
      Oligonukleotid spoT-rev

<400> SEQUENCE: 13
cctggcgagc atttc                                                      15

<210> SEQ ID NO 14
<211> LENGTH: 70
<212> TYPE: DNA
<213> ORGANISM: Artificial Sequence
<220> FEATURE:
<223> OTHER INFORMATION: Description of Artificial Sequence:
      Oligonukleotid recG-catfw

<400> SEQUENCE: 14
cctaccttcc tgccggatgc gattcatcac cctacaaatt caataaatta atgggaatta    60
gccatggtcc                                                            70

<210> SEQ ID NO 15
<211> LENGTH: 70
<212> TYPE: DNA
<213> ORGANISM: Artificial Sequence
<220> FEATURE:
<223> OTHER INFORMATION: Description of Artificial Sequence:
      Oligonukleotid gltS-catrev

<400> SEQUENCE: 15
ccgccgcaac aaagacaaat gcctgatacg cttcgcttat caagcctgcg gtgtaggctg    60
gagctgcttc                                                            70

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence:
      Oligonukleotid recG-fw

<400> SEQUENCE: 16
cgtcagacgg gtaatgc                                                    17

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence:
      Oligonukleotid gltS-rev

<400> SEQUENCE: 17
ggcgatggcg ttgatg                                                     16
```

PROCESS FOR THE FERMENTATIVE PRODUCTION OF HETEROLOGOUS PROTEINS BY MEANS OF ESCHERICHIA COLI

SEQUENCE LISTING

The text file is Sequence_listing.txt, created Feb. 9, 2010, and of size 44.2 KB, filed therewith, is hereby incorporated by reference.

CROSS REFERENCE TO RELATED APPLICATIONS

The application claims priority to German Application No. 10 2008 063 900.1, filed Dec. 19, 2008, the disclosure of which is hereby incorporated in its entirety.

BACKGROUND OF THE INVENTION

1. Field of the Invention

The present invention relates to a process for the fermentative production of heterologous proteins using an *Escherichia coli* strain having an attenuated (p)ppGpp-synthetase II activity.

2. Background Art

The market for recombinant protein pharmaceuticals (pharmaceutical proteins/biologics) has shown strong growth in recent years. Particularly important protein pharmaceuticals are eukaryotic proteins, especially mammalian proteins and human proteins. Examples of important pharmaceutical proteins (pharmaceutically active proteins) are cytokines, growth factors, protein kinase, protein hormones and peptide hormones, and antibodies and antibody fragments. Owing to the costs of producing pharmaceutical proteins, which are still very high, there is a continuous search for more efficient and therefore more cost-effective processes and systems for producing the proteins.

Recombinant proteins are usually produced either in mammalian cell cultures or in microbial systems. Microbial systems have the advantage over mammalian cell cultures in that recombinant proteins can be produced in this way more rapidly and with lower costs. Consequently, bacteria are especially suitable for producing recombinant proteins. The gram-negative enterobacterium *Escherichia coli* (*E. coli*) is currently the most frequently used organism for producing recombinant proteins, owing to its very well studied genetics and physiology, short generation time and easy manipulation. Production processes for recombinant proteins in *E. coli*, which involve the correctly folded target protein being secreted with high yield directly into the fermentation medium are particularly useful.

The literature has disclosed a number of *E. coli* strains and processes using *E. coli* strains, by which recombinant proteins are secreted into the fermentation medium. Thus, for example, US2008254511 describes various *E. coli* strains that have a mutation in the Braun lipoprotein (Lpp) gene and export the overproduced heterologous proteins into the medium.

In order to regulate and coordinate the metabolism under conditions, in which the cell is deficient of amino acids or the energy source, *E. coli* has a mechanism which is referred to as "stringent control". In this, the alarmones guanosine tetraphosphate (ppGpp) and guanosine pentaphosphate (pppGpp), usually combined as (p)ppGpp hereinbelow, play an important part as regulatory signal molecules, inter alia by slowing down the synthesis of stable RNAs (rRNA, tRNA) and enhancing expression of some amino acid biosynthesis genes, due to an increase in the (p)ppGpp level in the cell (Cashel et al., 1996, *Escherichia coli* and *Salmonella* Cellular and Molecular Biology, ed. Neidhardt, F. C. ASM Press, Washington, D.C. pp. 1458-1496). *E. coli* has two enzymes for synthesizing (p)ppGpp from ATP and GDP (ppGpp) and, respectively, ATP and GTP (pppGpp): (p)ppGpp synthetase I (PSI), encoded by the relA gene, is responsible for (p)ppGpp synthesis under stringent control, when the cells are subject to an amino acid deficiency. However, if cell growth is slowed down due to the primary carbon source being exhausted, (p)ppGPP is synthesized predominantly by (p)ppGpp synthetase II (PSII) which is encoded by the spoT gene. In contrast to PSI, the spoT gene product has also still a (p)ppGpp-3'-pyrophosphohydrolase activity in addition to the (p)ppGpp-synthetase activity, and accordingly can also actively control the cellular (p)ppGpp level by breaking down this compound (Gentry and Cashel, 1996, Mol. Microbiol. 19, 1373-84). The active sites of the two different catalytic activities of the PSII enzyme were shown to be non-identical but nevertheless located in close spatial proximity in the N-terminal region of the protein.

Both *E. coli* relA mutants and *E. coli* spoT mutants have been disclosed (Cashel et al., 1996, *Escherichia coli* and *Salmonella* Cellular and Molecular Biology, ed. Neidhardt, F. C. ASM Press, Washington, D.C. pp. 1458-1496). Strains having a relA1 mutation, with the IS2 insertion element being integrated in the relA gene sequence (relA::IS2), still possess a small residual PSI activity, whereas relA deletion mutants (ΔrelA) no longer have any PSI activity (Metzger et al., 1989, J. Biol. Chem. 264, 21146-52). In contrast to relA wild-type strains which have a functioning stringent control mechanism ("stringent" phenotype), relA mutants with a reduced or missing PSI activity exhibit a "relaxed" phenotype when encountering an amino acid deficiency situation. The latter phenotype manifests itself inter alia in that the cell is unable to accumulate (p)ppGpp above the basal level, and that the synthesis of stable RNA molecules is not stopped but continues undiminished. The basal level means the (p)ppGpp concentration range (10-30 pmol/$A_{450}$) for exponentially growing cells under non-limiting growth conditions (i.e. before encountering an amino acid deficiency situation), as disclosed in the literature (Cashel et al., 1996, *Escherichia coli* and *Salmonella* Cellular and Molecular Biology, ed. Neidhardt, F. C. ASM Press, Washington, D.C. pp. 1458-1496). Gitter et al. (1995, Appl. Microbiol. Biotechnol. 43, 89-92) have disclosed that the *E. coli* relA mutant CP79, in comparison with the relA wild-type strain CP78, increasingly releases into the culture medium proteins such as β-lactamase or interferonα1, which have been secreted into the periplasm under artificially induced amino acid deficiency conditions.

Depending on the extent of PSII activity impairment, strains with a mutation in the spoT gene have characteristic (p)ppGpp metabolic defects, inter alia: i) an increased basal ppGpp level during normal (balanced) growth, combined with a lower growth rate, ii) a higher induced ppGpp level during the stringent response, and iii) a lower ppGpp turnover rate after the stringent response has ended.

The DNA sequence of the *E. coli* spoT gene (SEQ ID NO: 1) codes for the spoT protein with the sequence SEQ ID NO: 2. The spoT gene is expressed as part of an operon which comprises the five genes gmk-rpoZ-spoT-spoU-recG. Expression of the operon and therefore also spoT expression are controlled firstly by the P1 promoter located upstream of the gmk gene, and secondly by the P2 promoter which is located in the gmk gene region coding for the C-terminal moiety (Cashel et al., 1996, *Escherichia coli* and *Salmonella*

Cellular and Molecular Biology, ed. Neidhardt, F. C. ASM Press, Washington, D.C. pp. 1458-1496). In strains with a spoT1 mutation (SEQ ID NO: 3), the spoT protein has an insertion of the two amino acids glutamine and aspartic acid downstream of the aspartic acid residue 84, and a histidine/tyrosine substitution in position 255 (Durfee et al., 2008, J. Bacteriol. 190, 2597-606). In addition, a number of spoT insertion or deletion mutants have also been described (Xiao et al., 1991, J. Biol. Chem. 266, 5980-90).

SUMMARY OF THE INVENTION

In at least one embodiment, the present invention provides a fermentative process for producing a heterologous protein utilizing an *E. coli* strain. The method of this embodiment comprises culturing an *E. coli* strain in a fermentation medium, the *E. coli* strain harboring a gene which codes for the heterologous protein and is functionally linked to a signal sequence coding for a signal peptide. The *E. coli* strain has an attenuated (p)ppGpp-synthetase II activity. The *E. coli* strain releases the heterologous protein into the fermentation medium.

DETAILED DESCRIPTION OF THE PREFERRED EMBODIMENT(S)

Reference will now be made in detail to presently preferred compositions, embodiments and methods of the present invention, which constitute the best modes of practicing the invention presently known to the inventors. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

The term "PSII activity" as used herein means the activity of an enzyme which can catalyze both (p)ppGpp synthesis and (p)ppGpp hydrolysis.

In an embodiment of the present invention provides, a fermentative process for producing a heterologous protein utilizing an *E. coli* strain is provided. The method of this embodiment comprises culturing an *E. coli* strain in a fermentation medium, the *E. coli* strain harboring a gene which codes for the heterologous protein and is functionally linked to a signal sequence coding for a signal peptide. The *E. coli* strain has an attenuated (p)ppGpp-synthetase II activity. The *E. coli* strain releases the heterologous protein into the fermentation medium.

In one refinement, an attenuated (p)ppGpp-synthetase II activity of an *E. coli* strain means that the *E. coli* strain has no more than 50% of the (p)ppGpp-synthetase II activity (PSII activity) of the *E. coli* strain prior to modification of its PSII activity, referred to as starting strain hereinbelow. In another refinement, an attenuated (p)ppGpp-synthetase II activity of an *E. coli* strain means that the *E. coli* strain has no more than 20% of the (p)ppGpp-synthetase II activity (PSII activity) of the *E. coli* strain prior to modification of its PSII activity, referred to as starting strain hereinbelow. In yest another refinement, attenuated PSII activity of a strain means the lack of PSII activity in the strain.

Methods of determining the synthetase and hydrolase activities of the PSII enzyme of a strain are known to the skilled worker (Mechold et al., 1996, J. Bacteriol. 178, 1401-1411). Moreover, processes for attenuating the PSII activity in a microorganism strain are known in the prior art. For example, the PSII activity can be attenuated by introducing a mutation (substitution, insertion or deletion of single or multiple nucleotides) into the reading frame of the spoT gene, the mutation causing a reduction in the activity of the enzyme. In addition, the PSII activity of a cell may also be attenuated by reducing expression of the spoT gene by mutating at least one element required for regulating expression (e.g. promoter, enhancer, ribosome binding site) by substituting, inserting or deleting single or multiple nucleotides. Such DNA sequences whose base sequence deviates from the sequence of the spoT wild-type gene due to mutations are also referred to as spoT alleles hereinbelow. The PSII activity can also be attenuated by completely deleting the spoT gene or its regulatory regions from the chromosome.

Those skilled in the art are familiar with processes for generating spoT alleles. For example, alleles of the spoT gene may be produced, by unspecific or specific mutagenesis using the spoT wild-type gene DNA as starting material. Unspecific mutations within the spoT gene or the promoter region of the spoT gene may be generated by chemical agents such as nitrosoguanidine, ethylmethanesulfonic acid and the like and/or by physical methods and/or by PCR reactions carried out under certain conditions. Methods of introducing mutations in specific positions within a DNA fragment have been disclosed. For example, one or more bases in a DNA fragment comprising the spoT gene and its promoter region can be substituted by means of PCR using suitable oligonucleotides as primers. It is also possible to produce the entire spoT gene or a new spoT allele by means of gene synthesis.

spoT alleles are normally generated in vitro first and then introduced into the chromosome of the cell, thereby replacing the originally present spoT wild-type gene and thus generating a spoT mutant of the strain. spoT alleles can be introduced into the chromosome of a host cell in place of the spoT wild-type gene/promoter by means of known standard methods, for example by means of the process, described in Link et al. (1997, J. Bacteriol. 179: 6228-37), for introducing chromosomal mutations into a gene via the mechanism of homologous recombination. For example, a chromosomal deletion of the entire spoT gene or of a part thereof can be introduced, with the aid of the λ-red recombinase system by the method described by Datsenko and Wanner (2000, Proc.

Natl. Acad. Sci. USA 97: 6640-5). spoT alleles may also be transferred by way of transduction by means of P1 phages or conjugation from a strain containing a spoT mutation to a spoT wild-type strain, with the spoT wild-type gene in the chromosome being replaced with the corresponding spoT allele. Aside from the described *E. coli* strains containing a spoT mutation, the skilled worker also knows methods of generating spoT mutants of any *E. coli* strains.

In one refinement, the spoT mutation is the spoT1 mutation or a spoT mutation resulting in attenuated PSII activity. In another refinement, the spoT mutation is given to a mutation which causes the complete loss of PSII activity.

In one variation, the *E. coli* strain used in the process of the invention has, in addition to the attenuated PSII activity, a mutation in the relA gene, which thereby results in a relaxed phenotype. An example of an relA mutation is the relA1 mutation or an relA mutation which causes a complete loss of PSI activity.

In another variation, the *E. coli* strain used in the process of the invention has a "leaky" mutation in addition to the attenuated PSII activity. A "leaky mutation" means a mutation in genes for structural elements of the outer cell membrane or the cell wall, selected from the group consisting of omp genes, tol genes, excD gene, excC gene, lpp gene, pal gene, env genes, and lky genes, which mutation causes the cells to increasingly discharge periplasmic proteins into the medium (Shokri et al., Appl. Microbiol. Biotechnol. 60 (2003), 654-664). In one refinement, the mutation is a "leaky" mutation in the lpp gene. In a further refinement, the mutation is a mutation selected from the group consisting of lpp1 mutation, lpp3 mutation and lpp deletion mutation. An lpp1 mutation is a mutation in the lpp gene, by which the arginine residue in position 77 is replaced with a cysteine residue, an lpp3 mutation is a mutation in the lpp gene, by which the glycine residue in position 14 is replaced with an aspartic acid residue. These mutations are described in detail in US2008254511. In a refinement, the lpp deletion mutation is a deletion of at least one nucleotide in the lpp gene itself or in the promoter region of the lpp gene, which mutation results in the cells having increased leakiness for periplasmic proteins.

Increased leakiness means for the purpose of the present invention that, after fermentation of the cells, the nutrient medium contains a higher concentration of periplasmic proteins, for example alkaline phosphatase, than with a fermentation of the *E. coli* strain W3110 (ATCC 27325) under the same conditions.

In a variation of the present invention, the *E. coli* strains have both a relaxed phenotype and a "leaky" mutation in addition to attenuated PSII activity.

The term "heterologous protein" as used herein means for a protein which is not part of the proteome, i.e. the entire natural set of proteins, of an *E. coli* K12 strain. All proteins naturally present in *E. coli* K12 strains can be derived from the known *E. coli* K12 genome sequence (Genbank Accession No. NC_000913). In one refinement, a heterologous protein produced in *E. coli* has more than 50% of the specific activity or effect (function) that is characteristic for the particular heterologous protein under natural conditions in the homologous host cell, or as obtained from homologous host cells. In another refinement, a heterologous protein produced in *E. coli* has more than 70% of the specific activity or effect (function) that is characteristic for the particular heterologous protein under natural conditions in the homologous host cell, or as obtained from homologous host cells. In another refinement, a heterologous protein produced in *E. coli* has more than 90% of the specific activity or effect (function) that is characteristic for the particular heterologous protein under natural conditions in the homologous host cell, or as obtained from homologous host cells.

In one refinement, the heterologous protein is a eukaryotic protein. In a further refinement, the heterologous protein contains one or more disulfide bridges or is a protein whose functional form is a dimer or multimer, i.e. the protein has a quaternary structure and is composed of a plurality of identical (homologous) or nonidentical (heterologous) subunits. Examples of eukaryotic proteins are antibodies and fragments thereof, cytokines, growth factors, protein kinases and protein hormones.

A particularly useful class of proteins consisting of a plurality of protein subunits comprises antibodies. Antibodies are widely used in research, diagnostics and as therapeutic agents, requiring particularly efficient, industrially feasible production processes.

In another variation of the invention, functional Fab antibody fragments and full-length antibodies are also extracellularly produced by means of the process of the invention. Useful full-length antibodies are antibodies of the IgG and IgM classes, in particular of the IgG class. When producing functional Fab antibody fragments, the cell must synthesize the corresponding fragment of the light chain (LC) comprising the $V_L$ and $C_L$ domains and of the heavy chain (HC) comprising the $V_H$ and CH1 domains simultaneously and then secrete them into the periplasm and finally into the fermentation medium. The two chains are then assembled outside the cytoplasm to give the functional Fab fragment. In a similar manner as to the production of the Fab fragments, the cell must synthesize the light and heavy chains of a full-length antibody simultaneously and then secrete them into the periplasm and finally into the fermentation medium. The two chains are then assembled outside the cytoplasm to give the functional full-length antibody.

The secretion of proteins from the cytoplasm into the periplasm requires the 5' end of the gene of the protein to be produced to be linked in frame to the 3' end of a signal sequence for protein export. Suitable for this purpose are in principle the genes of any signal sequences that enable the target protein in *E. coli* to be translocated with the aid of the Sec apparatus. Various signal sequences are described in the prior art, for example the signal sequences of the following genes: phoA, ompA, pelB, ompF, ompT, lamB, malE, staphylococcal protein A, StII and others (Choi and Lee, Appl. Microbiol. Biotechnol. 64 (2004), 625-635).

In various refinements of the present invention, the signal sequence of the *E. coli* phoA or ompA gene, or the signal sequence for a *Klebsiella pneumoniae* M5a1 cyclodextrin glycosyl transferase (CGTase), or the sequence derived from this signal sequence, which is disclosed in US2008076157 are used. In another refinement, the signal sequence, disclosed in EPO448093, for a *Klebsiella pneumoniae* M5a1 cyclodextrin glycosyl transferase (CGTase) with the sequence SEQ ID NO: 4 and to the sequence having sequence SEQ ID NO: 5, which is derived therefrom and disclosed in US2008076157 are utilized.

DNA molecules comprising an in-frame fusion of a signal sequence and the gene of the recombinant target protein are prepared by methods known to those skilled in the art. Therefore, it is possible to first amplify the gene of the target protein by means of PCR using oligonucleotides as primers, and then to link the gene by using common molecular-biological techniques to the DNA molecule which comprises the sequence of a signal peptide and which has been generated similarly to the gene of the target protein, so as to produce an in-frame fusion, i.e. a continuous reading frame comprising the signal sequence and the gene of the target protein. An alternative possibility is also that of preparing the entire DNA molecule comprising both functional segments mentioned above by means of gene synthesis. This signal sequence-recombinant gene fusion may then be either introduced into a vector, for example a plasmid, which is then introduced into the host cell by means of transformation, or integrated directly into the chromosome of the host cell by known methods. Introducing the signal sequence-recombinant gene fusion into a plasmid and transforming the host cell with the plasmid is found to be particularly useful.

The secretion of a protein consisting of a plurality of different subunits from the cytoplasm into the periplasm requires the genes of all subunits to be produced (target genes) to be functionally linked in each case with a signal sequence for protein export. The genes of the various subunits can be linked to different signal sequences or to the same signal sequence. Linkage to different signal sequences is found to be quite useful. For example, linking one subunit to the signal sequence of the *E. coli* phoA or ompA gene and linking a further subunit to the signal sequence for a *Klebsiella pneumoniae* M5a1 cyclodextrin glycosyl transferase (CGTase), having the sequence SEQ ID NO: 4 (EP0448093), or sequences derived therefrom, such as the sequence SEQ ID NO: 5 (US2008076157) is found to be particularly useful.

The signal sequence-target gene fusions of the individual subunits may then either be introduced into a vector, for example a plasmid, or be integrated directly into the chromosome of the host cell by known methods. The signal sequence-target gene fusions of the individual subunits may be cloned either on separate plasmids which are, however, compatible with one another, or on a single plasmid. The gene fusions may be combined in a single operon or they may be expressed in cistrons respectively separate from one another. Combining in a single operon is found to be particularly useful. Similarly, the two gene constructs may be combined in a single operon or integrated in cistrons respectively separate from each other into the chromosome of the host cell. One again, combining in a single operon is found to be particularly useful.

In one refinement, the DNA expression construct (signal sequence-target gene fusion), consisting of a signal sequence and a recombinant gene encoding the protein to be secreted, with expression signals functional in *E. coli* (promoter, transcription initiation site, translation initiation site, ribosome binding site, terminator) is provided. Suitable promoters are promoters known to those skilled in the art. Suitable examples of such promoters include, buat are not limited to, inducible promoters such as the lac, tac, trc, lambda PL, ara or tet promoters or sequences derived therefrom. In another refinement, expression may also be continuous by using a constitutive promoter such as, for example, the GAPDH promoter. It is also possible, however, to use the promoter normally linked to the gene of the recombinant protein to be produced.

This expression construct (promoter-signal sequence-recombinant gene) for the protein to be produced is then introduced into the cells having an attenuated PSII activity by applying methods known to the skilled worker (for example transformation). This is carried out, for example, on a vector, for example a plasmid, such as a derivative of known expression vectors such as pJF118EH, pKK223-3, pUC18, pBR322, pACYC184, pASK-IBA3 or pET. Suitable selection markers for plasmids are genes coding for a resistance to, for example, ampicillin, tetracycline, chloramphenicol, kanamycin or other antibiotics.

Thus, according to the invention, it is particularly useful to use an *E. coli* strain in which the recombinant gene is functionally linked to a signal sequence coding for a signal peptide active in *E. coli*, typically with expression signals functional in *E. coli*. In further refinements, the recombinant gene is functionally linked to a promoter, a transcription initiation site, translation initiation site, a ribosome binding site, and a terminator. Such expression signals are the expression signals mentioned above.

The cells having an attenuated PSII activity, which harbor a DNA expression construct consisting of a signal sequence and a recombinant gene encoding the protein to be secreted, linked to functional expression signals, are cultured (fermented) by customary fermentation processes known to the skilled worker in a bioreactor (fermenter). Fermentation is typically carried out in a customary bioreactor (e.g., a stirred tank, a bubble column fermenter, or an airlift fermenter). A stirred tank fermenter is found to be particularly useful.

The fermentation comprises culturing the cells of the protein production strain in a liquid medium over a period of 16-150 h, with various parameters such as, for example, nutrient supply, partial pressure of oxygen, pH and temperature of the culture being continuously monitored and precisely controlled. The culturing time is typically 24-72 hours. Suitable fermentation media are in principle all common media for culturing microorganisms that are known to those skilled in the art. Either complex media or minimal salt media supplemented with a defined proportion of complex components may be used. Examples of comples components include peptone, tryptone, yeast extract, molasses or corn steep liquor. For the production of pharmaceutical proteins, chemically defined salt media, that is media which, in contrast to complete medium, have a precisely defined substrate composition is found to be particularly useful.

In the process of the invention, the *E. coli* strain having an attenuated PSII activity and a gene encoding a heterologous protein (which gene is connected in frame to a signal sequence coding for a signal peptide functional in *E. coli*) grows to comparably high cell densities within a short fermentation time comparable to a strain having a PSII wild-type activity. During this process the heterologous protein is secreted into the salt medium.

The primary carbon source used for fermentation may be in principle any sugars, sugar alcohols or organic acids that can be utilized by the cells, or salts thereof. In a refinement, the carbon source is glucose, lactose or glycerol. Glucose and lactose are found to be particularly useful. A combined feed of a plurality of different carbon sources is also possible. The carbon source may be initially introduced to the fermentation medium at the start of the fermentation, either completely or partially, or nothing is introduced initially, and the carbon source is fed in the course of the fermentation. In one variation, one part of the carbon source is initially introduced while the other part is feed subsequently feed in. Particularly useful is the following: introducing the carbon source in a concentration of 10-30 g/l, commencing feeding when the concentration has fallen to less than 5 g/l, and carrying out the feeding so as to maintain the concentration at below 5 g/l.

The partial pressure of oxygen ($pO_2$) in the culture is typically between 10 and 70% saturation. In a refinement, the partial pressure of oxygen in the culture is between 30 and 60% saturation. In still another variation, the partial pressure of oxygen ($pO_2$) in the culture is between 45 and 55% saturation.

In one refinement, the pH of the culture is between pH 6 and pH 8. In another refinement, the temperature of the culture is maintained between 6.5 and 7.5. In another refinement, the temperature of the culture is maintained between 6.8 and 7.2.

In one refinement, the temperature of the culture is between 15 and 45° C. In another refinement, the temperature of the culture is between 20 and 40° C. In still another refinement, the temperature of the culture is between 25 and 35° C. In yet another embodiment, the temperature of the culture is about 30° C.

The secreted protein may be purified from the crude product by customary purification methods known to the skilled worker, as disclosed in the prior art. Usually, the cells are removed in a first step from the secreted target protein by separation methods such as centrifugation or filtration. The target protein may then be concentrated, for example by ultrafiltration, and is then purified further by standard methods such as precipitation, chromatography or ultrafiltration. Methods such as affinity chromatography, which utilizes the already correctly folded, native conformation of the protein are found to be particularly useful.

The following examples serve to further illustrate the invention. All of the molecular-biological and microbiological processes employed, such as polymerase chain reaction (PCR), gene synthesis, isolation and purification of DNA, modification of DNA by restriction enzymes, Klenow fragment and ligase, transformation, P1 transduction, etc., were carried out in the manner that is known to the skilled worker, described in the literature or recommended by the particular manufacturers.

EXAMPLE 1

Generation of a Chromosomal relA Deletion Mutant from an *E. coli* Wild-Type Strain (Comparative Example)

The prior art closest to the present invention is an *E. coli* strain which, owing to a relA mutation, has a reduced PSI activity and which, compared to a relA wild-type strain, increasingly releases into the culture medium proteins secreted into the periplasm, as described by Gitter et al. (1995, Appl. Microbiol. Biotechnol. 43, 89-92). A relA mutant was generated in order to demonstrate the advantage of strains having an attenuated PSII activity over this prior art.

For this purpose, the *E. coli* wild-type strain W3110 (American Type Culture Collection (ATCC) No. 27325) was mutated with the aid of the λ-Red recombinase according to the method of Datsenko and Wanner (2000, Proc. Natl. Acad. Sci. USA 97: 6640-5). First, a linear DNA fragment which includes a chloramphenicol resistance gene and which is flanked by in each case 50 base pairs of the 5' region and the 3' region, respectively, of the relA gene was generated with the aid of the polymerase chain reaction (PCR) using the oligonucleotides relAmut-fw (SEQ ID NO: 6) and relAmut-rev (SEQ ID NO: 7) as primers and the plasmid pKD3 (*Coli* Genetic Stock Center (CGSC) No. 7631) as template.

The W3110 strain was first transformed with the plasmid pKD46 (CGSC No. 7739). Competent cells of the strain obtained in this way, W3110 pKD46, which has been prepared according to the information by Datsenko and Wanner, were transformed with the abovementioned PCR-generated linear DNA fragment. Selection for integration of the chloramphenicol resistance cassette into the chromosome of W3110 in the position of the relA gene was carried out on LG-agar plates containing 20 mg/l chloramphenicol. In this way, cells were obtained, in which 95% of the coding region of the relA gene had been removed and replaced with the chloramphenicol resistance cassette. PCR using the oligonucleotides relA-fw (SEQ ID NO: 8) and relA-rev (SEQ ID NO: 9) and chromosomal DNA of the chloramphenicol-resistant cells as template was employed to confirm integration in the correct position in the chromosome. The cells were cured of the pKD46 plasmid by the procedure described (Datsenko and Wanner), and the strain generated in this way was referred to as W3110relA::cat.

The chloramphenicol resistance cassette was removed from the chromosome of the W3110relA::cat strain according to the protocol by Datsenko and Wanner with the aid of the pCP20 plasmid (CGSC No. 7629) carrying the FLP recombinase gene. The chloramphenicol-sensitive relA deletion mutant of W3110 finally obtained using the procedure was referred to as W3110ΔrelA.

EXAMPLE 2

Generation of a Chromosomal spoT Deletion Mutant from an *E. coli* ΔrelA strain

A spoT deletion mutant was generated from the *E. coli* strain W3110ΔrelA in principle as described for generating the strain W3110ΔrelA in Example 1.

The linear DNA fragment which includes a chloramphenicol resistance gene flanked by in each case base pairs of the 5' region and the 3' region, respectively, of the spoT gene was generated by using the oligonucleotides spoTmut-fw (SEQ ID NO: 10) and spoTmut-rev (SEQ ID NO: 11) as primers and the pKD3 plasmid as template. The strain W3110ΔrelA/pKD46 was transformed with the linear DNA fragment. Successful replacement of the spoT gene in the chromosome of W3110ΔrelA with the chloramphenicol resistance cassette was confirmed by means of PCR using the oligonucleotides spoT-fw (SEQ ID NO: 12) and spoT-rev (SEQ ID NO: 13) and chromosomal DNA of the chloramphenicol-resistant cells as template. The removal of the chloramphenicol resistance cassette from the chromosome by means of the procedure described in Example 1 produced the strain W3110ΔrelAΔspoT.

EXAMPLE 3

Introducing a Chromosomal spoT1 Mutation to Various *E. coli* Strains

A W3110ΔrelA mutant having the spoT1 allele (SEQ ID NO: 3; Durfee et al., 2008, J. Bacteriol. 190, 2597-606) was generated as an alternative to the ΔspoT mutant of W3110ΔrelA. For this purpose, the spoT1 allele was transferred from the strain K10 (Hfr PO2A tonA22 ompF626 relA1 pit-10 spoT1 T2(R); CGSC No. 4234) to the strain W3110ΔrelA by means of transduction using the phage P1. For this purpose, a chloramphenicol resistance cassette was first integrated into the chromosome of K10 approx. 2900 base pairs beyond the spoT gene, between the recG and gltS genes (recG-gltS::cat). The procedure was in principle as described in Example 1. A linear DNA fragment including a chloramphenicol resistance cassette which is flanked on each side by 50 base pairs of the recG-gltS intergenic region was generated by means of PCR using the oligonucleotides recG-catfw (SEQ ID NO: 14) and gltS-catrev (SEQ ID NO: 15) as primers and the pKD3 plasmid as template, and then transformed into the strain K10/pKD46. In this way, chloramphenicol-resistant clones were obtained, in which the resistance cassette has been integrated into the chromosome between the recG and gltS genes (K10recG-gltS::cat). Integration in the correct position was confirmed by means of PCR using the oligonucleotides recG-fw (SEQ ID NO: 16) and gltS-rev (SEQ ID NO: 17) and chromosomal DNA of the chloramphenicol-resistant cells as template. A P1 lysate was generated from the K10recG-gltS::cat strain according to the prior art, which lysate was then used to infect the W3110ΔrelA strain. This produced chloramphenicol-resistant transductands of W3110ΔrelA. The transduction process should transfer from K10recG-gltS::cat to W3110ΔrelA, aside from the resistance cassette, also the spoT1 allele which is located in close spatial proximity on the chromosome, with a theoretical rate of cotransduction of nearly 100%. That this was indeed the case was confirmed by amplification of the spoT gene by means of PCR using the oligonucleotides spoT-fw (SEQ ID NO: 12) and spoT-rev (SEQ ID NO: 13) and chromosomal DNA of the strain as template, and subsequent sequencing of the PCR product. Using the procedure described in Example 1 for removing the resistance cassette from the chromosome of the strain W3110ΔrelAspoT1recG-gltS::cat finally produced the strain W3110ΔrelAspoT1.

A similar procedure was used to introduce the spoT1 allele moreover also into the E. coli wild-type strain W3110. The resulting strain was referred to as W3110spoT1.

EXAMPLE 4

Introducing lpp "Leaky" Mutations to E. coli Strains Having an Attenuated PSII Activity Introducing an lpp3 mutation:
The lpp wild-type gene in the chromosome of the strains W3110ΔrelAΔspoT and W3110ΔrelAspoT1 was replaced with the lpp3 allele by way of homologous recombination. The strains W3110ΔrelAΔspoT1pp3 and W3110ΔrelAspoT11pp3, respectively, were generated by following a similar procedure as described in Example 3 of US2008254511. The strains obtained in this way were referred to as W3110ΔrelAΔspoT1pp3 and W3110ΔrelAspoT11pp3, respectively.
Introducing an lpp deletion mutation:
An lpp deletion was introduced into the chromosome of the strains W3110ΔrelAΔspoT and W3110ΔrelAspoT1 with the aid of the λ-Red recombinase system by the method of Datsenko and Wanner (2000, Proc. Natl. Acad. Sci. USA 97: 6640-5), the procedure being similar to Example 1 of US2008254511. The strains obtained in this way were referred to as W3110ΔrelAΔspoTΔ1pp and W3110ΔrelAspoT1Δ1pp, respectively.

EXAMPLE 5

Fermentative Production of a Cyclodextrin Glycosyl Transferase on a 10 l Scale, using Strains Having an Attenuated PSII Activity For production of Klebsiella pneumoniae M5a1 cyclodextrin glycosyl transferase (CGTase) on a 10 l scale, the strains W3110ΔrelA, W3110spoT1, W3110ΔrelAΔspoT, W3110ΔrelAspoT1, W3110ΔrelAΔspoTΔ1pp, W3110ΔrelAΔspoT1pp3, W3110ΔrelAspoT1Δ1pp and W3110ΔrelAspoT11pp3 were transformed with the pCGT plasmid by means of the CaCl₂ method. Selection for plasmid-containing cells was performed using ampicillin (100 mg/l).

The pCGT plasmid contains, aside from the gene for resistance to ampicillin, inter alia also the CGTase structural gene, including the native CGTase signal sequence. Expression of the CGTase gene is under the control of the tac promoter. The pCGT plasmid is described in Example 4 of US2008254511.

CGTase was produced in 10 l stirred tank fermenters, using the strains W3110ΔrelA/pCGT, W3110spoT1/pCGT, W3110ΔrelAΔspoT/pCGT, W3110ΔrelAspoT1/pCGT, W3110ΔrelAΔspoTΔ1pp/pCGT, W3110ΔrelAΔspoT1pp3/pCGT, W3110ΔrelAspoT1Δ1pp/pCGT and W3110ΔrelAspoT11pp3/pCGT.

The fermenter, to which 6 l of FM4 fermentation medium was introduced (1.5 g/l $KH_2PO_4$; 5 g/l $(NH_4)_2SO_4$; 0.5 g/l $MgSO_4 \times 7\ H_2O$; 0.15 g/l $CaCl_2 \times 2\ H_2O$, 0.075 g/l $FeSO_4 \times 7\ H_2O$; 1 g/l $Na_3$ citrate$\times 2\ H_2O$; 0.5 g/l NaCl; 1 ml/l trace element solution (0.15 g/l $Na_2MoO_4 \times 2\ H_2O$; 2.5 g/l $Na_3BO_3$; 0.7 g/l $CoCl_2 \times 6\ H_2O$; 0.25 g/l $CuSO_4 \times 5\ H_2O$; 1.6 g/l $MnCl_2 \times 4\ H_2O$; 0.3 g/l $ZnSO_4 \times 7\ H_2O$); 5 mg/l vitamin $B_1$; 3 g/l phytone; 1.5 g/l yeast extract; 10 g/l glucose; 100 mg/l ampicillin), was inoculated at a ratio of 1:10 with a preculture cultured overnight in the same medium. During fermentation, the temperature was set to 30° C. and the pH was kept constant at pH 7.0 by metering in $NH_4OH$ or $H_3PO_4$. Glucose was metered in throughout the fermentation, aiming at a maximum glucose concentration in the fermentation medium of <10 g/l. Expression was induced by adding isopropyl β-D-thiogalactopyranoside (IPTG) to 0.1 mM at the end of the logarithmic growth phase.

After 72 h of fermentation, samples were removed, the cells were removed from the fermentation medium by centrifugation, and the CGTase content in the fermentation supernatant was determined by the following activity assay:

Assay buffer: 5 mM Tris-HCl-buffer>pH 6.5, 5 mM $CaSO_4$.2 $H_2O$

Substrate: 10% strength Noredux solution in assay buffer (pH 6.5)

Assay mix: 1 ml of substrate solution+1 ml of centrifuged and, where appropriate, diluted culture supernatant (5 min, 12 000 rpm)+3 ml of methanol Reaction temperature: 40° C.

Enzyme Assay:
 Preheating the solutions (approx. 5 min at 40° C.)
 Adding the enzyme solution to the substrate solution; rapid mixing (Whirl Mixer)
 Incubating at 40° C. for 3 min
 Stopping the enzyme reaction by adding methanol; rapid mixing (Whirl Mixer)
 Cooling the reaction mix on ice (approx. 5 min)
 Centrifuging (5 min, 12 000 rpm) and pipetting off the clear supernatant
 Analyzing the CD produced by means of HPLC Enzyme activity: A=G*V1*V2/(t*MG) (units/ml)

A=activity

G=CD content in mg/l=assay mix: unit areas×$10^4$/standard solution (10 mg/ml)/unit areas V1=dilution factor in the assay mix (carrying out the above-mentioned instructions: V1=5)

V2=dilution factor of the culture supernatant prior to use in the assay; when undiluted: V2=1 t=reaction time in min

MG=molecular weight in g/mol (CD=973 g/mol)

1 unit=1 μmol of product/min

The amount of CGTase present in the fermentation supernatant can be calculated from the CGTase activity determined in this way, with 150 U/ml CGTase activity corresponding to about 1 g/l CGTase protein. Table 1 depicts the cyclodextrin glycosyl transferase yields obtained in each case.

TABLE 1

Cyclodextrin glycosyl transferase yields in the fermentation supernatant after 72 hours of fermentation

| Strain | CGTase (U/ml) | CGTase (g/l) |
|---|---|---|
| W3110ΔrelA/pCGT | 220 | 1.5 |
| W3110spoT1/pCGT | 260 | 1.7 |
| W3110ΔrelAΔspoT/pCGT | 340 | 2.3 |
| W3110ΔrelAspoT1/pCGT | 360 | 2.4 |
| W3110ΔrelAΔspoTΔ1pp/pCGT | 530 | 3.5 |
| W3110ΔrelAspoT1Δ1pp/pCGT | 540 | 3.6 |
| W3110ΔrelAΔspoT1pp3/pCGT | 530 | 3.5 |
| W3110ΔrelAspoT11pp3/pCGT | 550 | 3.7 |

EXAMPLE 6

Fermentative Production of a Hirudin Derivative on a 10 l Scale, Using Strains Having an Attenuated PSII Activity This example describes the fermentative production of a hirudin derivative with the N-terminal amino acid sequence Ala-Thr-Tyr-Thr-Asp. To produce the hirudin derivative, the strains W3110ΔrelA, W3110spoT1, W3110ΔrelAΔspoT, W3110ΔrelAspoT1, W3110ΔrelAΔspoTΔ1pp, W3110ΔrelAΔspoT1pp3, W3110ΔrelAspoT1Δ1pp and W3110ΔrelAspoT11pp3 were first transformed in each case with the pCMT203 plasmid by means of the $CaCl_2$ method. Selection for plasmid-containing cells was performed using ampicillin (100 mg/l).

The pCMT203 plasmid includes, aside from the gene for resistance to ampicillin, inter alia also the structural gene of the hirudin derivative, which is fused in frame to the 3' end of a CGTase signal sequence. Expression of the CGTase signal sequence-hirudin fusion is under the control of the tac promoter. The pCMT203 plasmid is described in EP0448093.

The hirudin derivative was produced on a 10 l scale in a process similar to that described in Example 5, using the strains w3110ΔrelA/pCMT203, W3110spoT1/pCMT203, W3110ΔrelAΔspoT/pCMT203, W3110ΔrelAspoT1/pCMT203, W3110ΔrelAΔspoTΔ1pp/pCMT203, W3110ΔrelAΔspoT1pp3/pCMT203, W3110ΔrelAspoT1Δ1pp/pCMT203 and W3110ΔrelAspoT11pp3/pCMT203. After 72 h of fermentation, samples were taken, the cells were then removed by centrifugation from the fermentation medium and the hirudin content in the fermentation supernatant was determined by means of a thrombin inactivation assay, as described in Chang (1991, J. Biol. Chem. 266, 10839-43), with 16 000 antithrombin (AT) units/ml hirudin activity corresponding to about 1 g/l hirudin protein. Table 2 depicts the hirudin yields achieved in each case in the fermentation supernatant.

TABLE 2

Hirudin yield (in AT U/ml and g/l) in the fermentation supernatant after 72 h of fermentation

| Strain | Hirudin (AT U/ml) | Hirudin (g/l) |
|---|---|---|
| W3110ΔrelA/pCMT203 | 1000 | 0.06 |
| W3110spoT1/pCMT203 | 1400 | 0.09 |
| W3110ΔrelAΔspoT/pCMT203 | 2500 | 0.16 |
| W3110ΔrelAspoT1/pCMT203 | 2800 | 0.18 |
| W3110ΔrelAΔspoTΔ1pp/pCMT203 | 52 000 | 3.25 |
| W3110ΔrelAspoT1Δ1pp/pCMT203 | 54 000 | 3.38 |
| W3110ΔrelAΔspoT1pp3/pCMT203 | 53 000 | 3.31 |
| W3110ΔrelAspoT11pp3/pCMT203 | 56 000 | 3.50 |

EXAMPLE 7

Fermentative Production of Interferonα2b on a 10 l Scale, Using Strains Having an Attenuated PSII Activity To produce interferonα2b, the strains W3110ΔrelA, W3110spoT1, W3110ΔrelAΔspoT, W3110ΔrelAspoT1, W3110ΔrelAΔspoTΔ1pp, W3110ΔrelAΔspoT1pp3, W3110ΔrelAspoT1Δ1pp and W3110ΔrelAspoT11pp3 were transformed in each case with the pIFN plasmid according to the $CaCl_2$ method. Selection for plasmid-containing cells was performed using ampicillin (100 mg/l).

The pIFN plasmid includes, aside from the gene for resistance to ampicillin, inter alia also the interferonα2b structural gene which is fused in frame to the 3' end of a CGTase signal sequence. Expression of the CGTase signal sequence-interferonα2b fusion is under the control of the tac promoter. The pIFN plasmid is described in Example 6 of US2008254511.

Interferonα2b was produced on a 10 l scale in a process similar to that described in Example 5, using the strains W3110ΔrelA/pIFN, W3110spoT1/pIFN, W3110ΔrelAΔspoT/pIFN, W3110ΔrelAspoT1/pIFN, W3110ΔrelAΔspoTΔ1pp/pIFN, W3110ΔrelAΔspoT1pp3/pIFN, W3110ΔrelAspoT1Δ1pp/pIFN and W3110ΔrelAspoT11pp3/pIFN. After 72 h of fermentation, samples were taken, the cells were then removed by centrifugation from the fermentation medium, and the interferonα2b content in the fermentation supernatant was determined.

For this purpose, the proteins in the fractionated electrophoretically in an SDS polyacrylamide gel and, by means of detection in an immunoblot with anti-interferon-specific antibodies, quantified as follows: 1 μl of supernatant was admixed with sample buffer (2×Tris SDS-Sample Buffer (Invitrogen Cat. No. LC2676): 0.125 M Tris.HCl, pH 6.8, 4% w/v SDS, 20% v/v glycerol, 0.005% v/v bromophenol blue, 5% beta-mercaptoethanol). Moreover, defined amounts of interferonα2b were co-applied as standard. The proteins were denatured by heating to 100° C. for 5 min, cooling on ice for 2 min, and centrifuging.

The proteins were fractionated by electrophoresis in a 12% NuPAGE® Bis-Tris gel (Invitrogen Cat. No. NP0341) with 1×MES-containing running buffer (Invitrogen Cat. No. NP0002) (electrophoresis parameters: 40 min at 200 V). Detection and quantification via immunoblot were carried out according to the following protocol:

Transfer by Wet Blotting
Module: Amersham: Hoefer TE 22 Mini Tank Transfer Unit, Code Number: 80-6204-26
Membrane: nitrocellulose membrane (Schleicher & Schuell, BA 85, cellulose nitrate (E), 0.45 μm pore size)
Cut Whatman filter and nitrocellulose membrane to a suitable size and soak in transfer buffer (Invitrogen Cat. No. LC3675) using pieces of foam (sponges), without air bubbles.

Assembly of the sandwich: black grid, connection to the cathode, 2 sponges, each 3 mm thick, Whatman paper, SDS polyacrylamide gel, NC membrane, Whatman, 1 sponge, 6 mm thick, white grid, connection to the anode.
Transfer conditions: I=200 mA constant current, U=unlimited, running time 60 min
Prehybridization
  Incubation of the membrane in 25 ml of prehybridization buffer
    Swirl at RT for 30 min
Hybridization of 1$^{st}$ Antibody
  Incubation of the membrane in 25 ml of prehybridization buffer+0.15 μg/ml (→3.75 μg) anti-human IFN-alpha antibody (Pepro Tech EC, through Biazol Cat. No. 500-P32A)
    Swirl at RT for 90 min or overnight.
Washing
  Swirl with 1×PBS for 10 seconds, RT, pour off buffer
  Swirl with 1×PBS for 2×15 min, RT, pour off buffer
Hybridization of 2$^{nd}$ Antibody
  Incubation of the membrane in 25 ml of prehybridization buffer+25 μl (1:1000) goat anti-rabbit IgG horseradish peroxidase conjugate (HRP) (Southern Biotech, through Biazol Cat. No. 4050-05)
    Swirl at RT for 60 min
Washing
  Swirl with 1×PBS for 10 seconds, RT, pour off buffer
  Swirl with 1×PBS for 2×15 min, RT, pour off buffer
Detection Via Chemiluminescence
  Prepare Lumi-Light Western blotting substrate (Roche, Cat. No. 2015200): mix Lumi-Light luminol/enhancer solution and Lumi-Light stable peroxide solution in a 1:1 ratio: 3 ml/NC membrane. Incubate blot with Lumi-Light Western blotting substrate at RT for 5 min, drain off excess, cover membrane with Saran wrap and immediately lay on an X-ray film (Kodak, X-OMAT), expose for 2 min, develop and fix. If the signals are weak, exposure is repeated over a longer period.
Buffer
Prehybridization buffer: 5% skimmed milk powder in 1×PBS
10×PBS: 100 mM $NaH_2PO_4$, 1.5 M NaCl, pH 7.5 with NaOH, 0.5% Triton 100
1×PBS: dilute 10×PBS 1:10 with deionized water
Quantification
  Quantitative evaluation was carried out, after scanning in the immunoblot using a Biorad GS-800 calibrated densitometer, by means of Quantity One 1-D-Analysis software (Biorad), by way of comparison with the applied standard.
  The interferonα2b yields determined in this way in the fermentation supernatant are depicted in Table 3.

TABLE 3

Interferonα2b yields in the fermentation supernatant after 72 h of fermentation

| Strain | Interferonα2b (mg/l) |
|---|---|
| W3110ΔrelA/pIFN | 10 |
| W3110spoT1/pIFN | 20 |
| W3110ΔrelAΔspoT/pIFN | 40 |
| W3110ΔrelAspoT1/pIFN | 50 |
| W3110ΔrelAΔspoTΔ1pp/pIFN | 580 |
| W3110ΔrelAspoT1Δ1pp/pIFN | 600 |
| W3110ΔrelAΔspoT1pp3/pIFN | 590 |
| W3110ΔrelAspoT11pp3/pIFN | 610 |

EXAMPLE 8

Fermentative Production of Fab Antibody Fragments on a 10 l Scale, Using Strains Having an Attenuated PSII Activity The present example describes production of a Fab fragment of the well-characterized anti-lysozyme antibody D1.3.
To produce the anti-lysozyme Fab fragment, the strains W3110ΔrelA, W3110spoT1, W3110ΔrelAΔspoT, W3110ΔrelAspoT1, W3110ΔrelAΔspoTA1pp, W3110ΔrelAΔspoT1pp3, W3110ΔrelAspoT1Δ1pp and W3110ΔrelAspoT11pp3 were transformed in each case with the plasmid pFab-Anti-Lysozym, using the $CaCl_2$ method. Selection for plasmid-containing cells was performed using ampicillin (100 mg/l).

The pFab-Anti-Lysozym plasmid includes, aside from the gene for resistance to ampicillin, inter alia also the structural genes of the HC and LC of the Fab fragment by way of an operon. The HC here is fused in frame to the 3' end of the ompA signal sequence (ompA$^{SS}$) and the LC is fused in frame to the 3' end of a CGTase signal sequence (CGT$^{SS}$). Expression of the ompA$^{SS}$-HC-CGT$^{SS}$-LC-operon is under the control of the tac promoter. The pFab-Anti-Lysozym plasmid is described in Example 7 of US2008254511.

The anti-lysozyme Fab fragment was produced on the 10 l scale in a process similar to that described in Example 5, using the strains W3110ΔrelA/pFab-Anti-Lysozym, W3110spoT1/pFab-Anti-Lysozym, W3110ΔrelAΔspoT/pFab-Anti-Lysozym, W3110ΔrelAspoT1/pFab-Anti-Lysozym, W3110ΔrelAΔspoTΔ1pp/pFab-Anti-Lysozym, W3110ΔrelAΔspoT1pp3/pFab-Anti-Lysozym, W3110ΔrelAspoT1Δ1pp/pFab-Anti-Lysozym and W3110ΔrelAspoT11pp3/pFab-Anti-Lysozym. After 72 h of fermentation, samples were taken and the cells were then removed from the fermentation medium by centrifugation.

The anti-lysozyme Fab fragment was purified from the fermentation supernatants by means of affinity chromatography as described in Skerra (1994, Gene 141, 79-84).

Quantification and determination of the activity of the purified anti-lysozyme Fab fragment was carried out using an ELISA assay with lysozyme as antigen (Skerra, 1994, Gene 141, 79-84).

Table 4 lists the yields of functional anti-lysozyme Fab fragment, which were isolated in each case from 20 ml of fermentation supernatant after fermentation for 72 h.

TABLE 4

Anti-lysozyme Fab fragment yields in the fermentation supernatant after 72 h of fermentation

| Strain | Anti-lysozyme Fab fragment purified from 20 ml of supernatant [mg] | Anti-lysozyme Fab fragment yield [g/l] in the fermentation supernatant (extrapolated) |
|---|---|---|
| W3110ΔrelA/ pFab-Anti-Lysozym | 0.5 | 0.03 |
| W3110spoT1/ pFab-Anti-Lysozym | 1 | 0.05 |
| W3110ΔrelAΔspoT/ pFab-Anti-Lysozym | 4 | 0.20 |
| W3110ΔrelAspoT1/ pFab-Anti-Lysozym | 3 | 0.15 |
| W3110ΔrelAΔspoTΔ1pp/ pFab-Anti-Lysozym | 32 | 1.60 |

TABLE 4-continued

Anti-lysozyme Fab fragment yields in the fermentation supernatant after 72 h of fermentation

| Strain | Anti-lysozyme Fab fragment purified from 20 ml of supernatant [mg] | Anti-lysozyme Fab fragment yield [g/l] in the fermentation supernatant (extrapolated) |
|---|---|---|
| W3110ΔrelAspoT1Δ1pp/pFab-Anti-Lysozym | 36 | 1.80 |
| W3110ΔrelAΔspoT1pp3/pFab-Anti-Lysozym | 34 | 1.7 |
| W3110ΔrelAspoT11pp3/pFab-Anti-Lysozym | 37 | 1.85 |

EXAMPLE 9

Fermentative Production of Full-Length Antibodies on a 10 l Scale, Using Strains Having an Attenuated PSII Activity The present example describes production of the anti-tissue factor (αTF) IgG1 antibody.

To produce the anti-αTF antibody, the strains W3110ΔrelA, W3110spoT1, W3110ΔrelAΔspoT, W3110ΔrelAspoT1, W3110ΔrelAΔspoTΔ1pp, W3110ΔrelAΔspoT1pp3, W3110ΔrelAspoT1Δ1pp and W3110ΔrelAspoT11pp3 were transformed in each case with the plasmid pAK-Anti-TF, using the CaCl$_2$ method. Selection for plasmid-containing cells was carried out using ampicillin (100 mg/l).

The pAK-Anti-TF plasmid includes, aside from the gene for resistance to ampicillin, inter alia also the structural genes of the HC and LC of the anti-αTF antibody by way of an operon. The HC here is fused in frame to the 3' end of the ompA signal sequence (ompA$^{SS}$) and the LC is fused in frame to the 3' end of a CGTase signal sequence (CGT$^{SS}$). Expression of the ompA$^{SS}$-HC-CGT$^{SS}$-LC-operon is under the control of the tac promoter. The pAK-Anti-TF plasmid is described in Example 8 of US2008254511.

The anti-αTF antibody is produced on the 10 l scale in a process similar to that described in Example 5, using the strains W3110ΔrelA/pAK-Anti-TF, W3110spoT1/pAK-Anti-TF, W3110ΔrelAΔspoT/pAK-Anti-TF, W3110ΔrelAspoT1/pAK-Anti-TF, W3110ΔrelAΔspoTΔ1pp/pAK-Anti-TF, W3110ΔrelAΔspoT1pp3/pAK-Anti-TF, W3110ΔrelAspoT1Δ1pp/pAK-Anti-TF and W3110ΔrelAspoT11pp3/pAK-Anti-TF. After 72 h of fermentation, samples were taken and the cells were then removed from the fermentation medium by centrifugation.

The anti-αTF antibody secreted into the fermentation medium was quantified by determining the activity using an ELISA assay with soluble tissue factor as antigen (coating) and a peroxidase-conjugated goat anti-human F(ab')$_2$ fragment as secondary antibody, as described in Simmons et al. (2002, J. Immunol. Methods 263, 133-47).

Table 5 lists the yields of functional anti-αTF antibody determined in this way.

TABLE 5

Anti-αTF antibody yields in the fermentation supernatant after 72 h of fermentation

| Strain | Anti-αTF antibody [mg/l] |
|---|---|
| W3110ΔrelA/pAK-Anti-TF | 8 |
| W3110spoT1/pAK-Anti-TF | 11 |
| W3110ΔrelAΔspoT/pAK-Anti-TF | 21 |
| W3110ΔrelAspoT1/pAK-Anti-TF | 18 |
| W3110ΔrelAΔspoTΔ1pp/pAK-Anti-TF | 680 |
| W3110ΔrelAspoT1Δ1pp/pAK-Anti-TF | 660 |
| W3110ΔrelAΔspoT1pp3/pAK-Anti-TF | 670 |
| W3110ΔrelAspoT11pp3/pAK-Anti-TF | 670 |

What is claimed is:

1. A process for producing a heterologous protein, the process comprising:
   culturing an *E. coli* strain in a fermentation medium including a primary carbon source, the *E. coli* strain harboring a gene which codes for the heterologous protein and is functionally linked to a signal sequence coding for a signal peptide, the *E. coli* strain having an attenuated (p)ppGpp-synthetase II activity (PSII activity);
   releasing the heterologous protein into the fermentation medium; and
   removing the heterologous protein from the fermentation medium.

2. The process of claim 1, wherein the *E. coli* strain has no more than 50% of the PSII activity of the strain prior to modification of its PSII activity.

3. The process of claim 1, wherein the *E. coli* strain has no more than 20% of the PSII activity of the strain prior to modification of its PSII activity.

4. The process of claim 1, wherein the heterologous protein is a eukaryotic protein.

5. The process of claim 1, wherein the signal sequence is the signal sequence of the *E. coli* phoA or ompA gene.

6. The process of claim 1, wherein the signal sequence is the signal sequence for a *Klebsiella pneumoniae* M5a1 cyclodextrin glycosyltransferase (CGTase).

7. The process of claim 1, wherein the signal sequence is the sequence derived from this signal sequence, SEQ ID NO: 5.

* * * * *